ND

(12) United States Patent  
Ramirez

(10) Patent No.: US 6,705,328 B1  
(45) Date of Patent: Mar. 16, 2004

(54) METHODS TO IMPREGNATE AND DISPENSE FLOSS USING NOVEL DENTAL FLOSS DISPENSERS

(76) Inventor: Josè E. Ramirez, 15 Fox Ct., Trumbull, CT (US) 06611

( * ) Notice: Subject to any disclaimer, the term of this patent is extended or adjusted under 35 U.S.C. 154(b) by 51 days.

(21) Appl. No.: 09/994,486

(22) Filed: Nov. 27, 2001

(51) Int. Cl.[7] ............................................. A61C 15/00
(52) U.S. Cl. ........................ 132/322; 132/324; 132/323
(58) Field of Search .................. 132/322, 323, 132/324, 325, 326, 327, 328, 329

(56) References Cited

U.S. PATENT DOCUMENTS

| | | | |
|---|---|---|---|
| 3,830,247 A | | 8/1974 | Kaphalakos |
| 3,942,539 A | | 3/1976 | Corliss et al. |
| 4,019,522 A | * | 4/1977 | Elbreder ................... 132/322 |
| 4,162,688 A | | 7/1979 | Tarrson et al. |
| 4,673,106 A | | 6/1987 | Fishman ................... 222/80 |
| 5,020,694 A | | 6/1991 | Pettengill |
| 5,065,861 A | | 11/1991 | Greene et al. |
| 5,076,302 A | | 12/1991 | Chari |
| 5,582,195 A | | 12/1996 | Nagel |
| 5,873,495 A | | 2/1999 | Saint-Germain |
| 5,896,868 A | | 4/1999 | Kyte |

* cited by examiner

*Primary Examiner*—John J. Wilson  
*Assistant Examiner*—Robyn Kieu Doan  
(74) *Attorney, Agent, or Firm*—Carter, DeLuca, Farrell & Schmidt, LLP

(57) ABSTRACT

Improved dental floss dispensers that impregnate floss with fluids and/or solids have been developed. One dental floss dispenser consists of a tube that holds a roll of dental floss separated from the main chamber by either a disc or a bag. The main chamber may consist of one or several compartments and it is filled with fluids and/or solids. The untreated floss is first threaded through a hole in the protective cover that separates the floss reel from the lower compartment and it passes through the lower compartment filled with a viscous fluid of sufficiently high viscosity. The partially impregnated floss is then threaded through a barrier that divides the lower and the upper compartments and passes through the upper compartment filled with an impregnating fluid or solid. The fluids and/or solids are now adhered to the floss so it can be used as a means to deliver compositions. The impregnated floss is then threaded through a hole in the closure of the dispenser and it is sealed by adhesive backed plastic, paper or foil. A cutter is placed on the neck of the container and it is used for removing a segment of the impregnated dental floss. A second dental floss dispenser consists of separate compartments placed in a chamber. Each compartment contains a fluid or a solid in addition to the floss dispensed. The individually impregnated flosses are then brought in close contact through a narrow tube. The fluid in one of the flosses has a gel consistency that allows the other floss impregnated with a fluid or a solid to adhere to the floss so it can be used as a means to deliver compositions that when placed in contact with each other are unstable. The impregnated floss can then be used in areas between the teeth for the treatment of gingivitis, prevention of cavities and for other purposes such as rubbing against the teeth for whitening.

7 Claims, 8 Drawing Sheets

METHODS TO IMPREGNATE AND DISPENSE FLOSS USING NOVEL DENTAL FLOSS DISPENSERS

BACKGROUND

1. Technical Field

The invention relates generally to improved dental floss dispensers that apply at least one fluid and optionally one or more solids to the dental floss during removal of the floss from the dispenser. The consistency of the fluid allows it to adhere to the floss. In certain embodiments, two fluids are used which preferably can adhere to each other. In another embodiment, a fluid and a solid are used, and the fluid causes adherence of the solid to the floss as it is withdrawn from the dispenser.

2. Background of Related Art

Various conventional dental floss dispensers are available. Examples include the dispensers disclosed in U.S. Pat. No. 5,873,495 , U.S. Pat. No. 5,065,861 and U.S. Pat. No. 3,942,539. Certain floss dispensers have been designed to provide application of material to the floss as it is withdrawn from the dispenser. Examples include the dispensers disclosed in U.S. Pat. No. 3,830,247, U.S. Pat. No. 4,126,688, U.S. Pat. No. 5,076,302 , U.S. Pat. No. 5,582,195 and U.S. Pat. No. 5,896,868. U.S. Pat. No. 5,020,694 discloses a multi-cavity piston-type toothpaste dispenser. Each of the foregoing nine patents is incorporated in its entirety herein by reference.

It would be advantageous to provide a floss dispenser which does not leak the substance being applied to the floss. It would also be desirable to provide an impregnated dental floss or flosses with individually incompatible chemical components that can be utilized between the teeth for the treatment of gingivitis, the prevention of cavities and on the teeth for whitening.

SUMMARY

A dental floss dispenser has now been designed that includes a housing having an opening through which dental floss can be dispensed. First and second chambers are defined within the housing. The first and second chambers contain respective first and second compositions that can be chemically different from each other or even chemically incompatible. At least one supply of dental floss is disposed within the housing and positioned such that the floss dispensed through the opening in the housing has the first and second compositions applied thereto. In one embodiment, the housing is a tube and chambers are defined therein by dividers. In another embodiment, the housing contains two containers that each define a chamber, with each chamber containing a supply of dental floss and a composition to be applied to the floss. Means, such as, for example, a funneling tube, urges the floss from one chamber into contact with floss from the other chamber prior to dispensing.

The compositions applied to the floss can be in the form of a fluid, preferable a viscous fluid such as, for example, a gel or paste, or a solid, such as, for example, a powder. Combinations of fluid and solid compositions can also be used.

BRIEF DESCRIPTION OF THE DRAWING FIGURES

The present floss dispensers may be embodied in the forms illustrated in the accompanying drawings, attention being called to the facts, however, that the drawings are illustrative only, and that changes may be made in the specific construction illustrated and described within the scope of the appended claims.

DETAILED DESCRIPTION OF THE PREFERRED EMBODIMENTS

Figure 1:
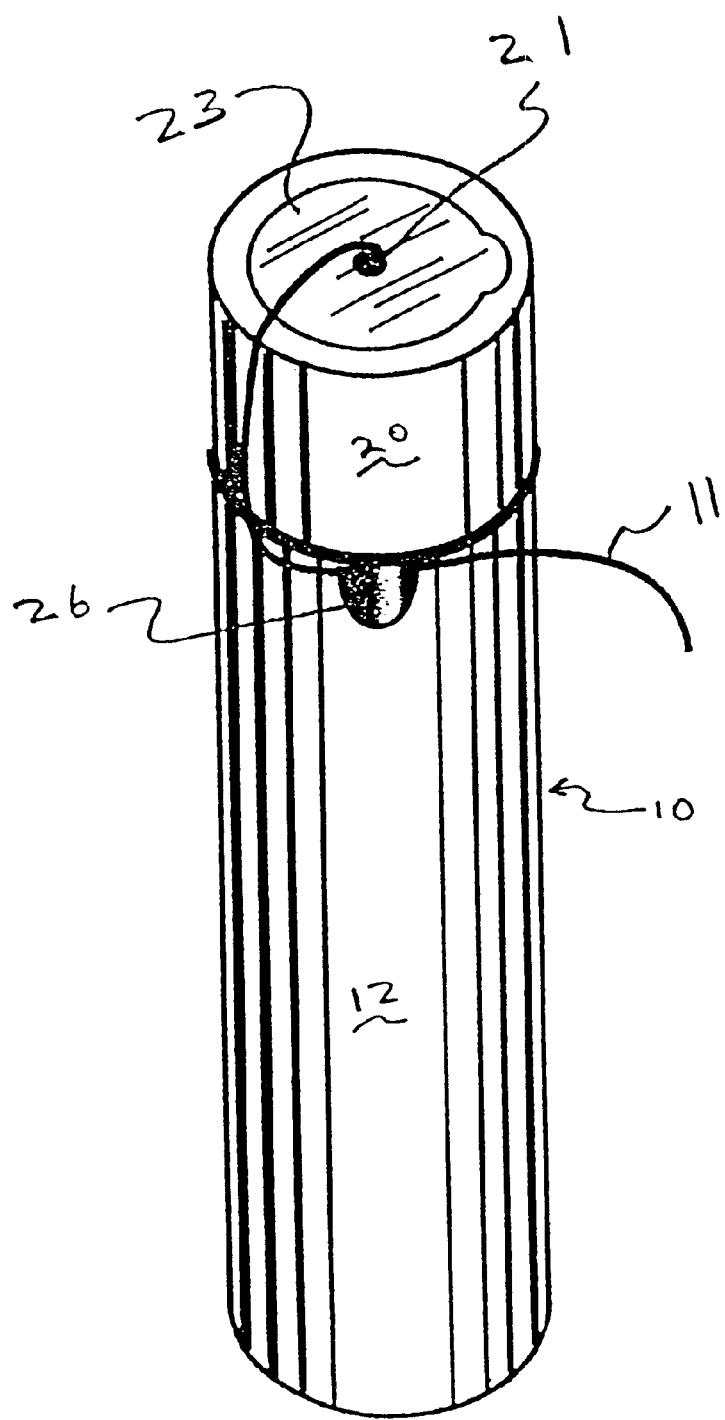
FIG. 1 is a perspective view of a floss dispenser in accordance with this disclosure.
Figure 2:
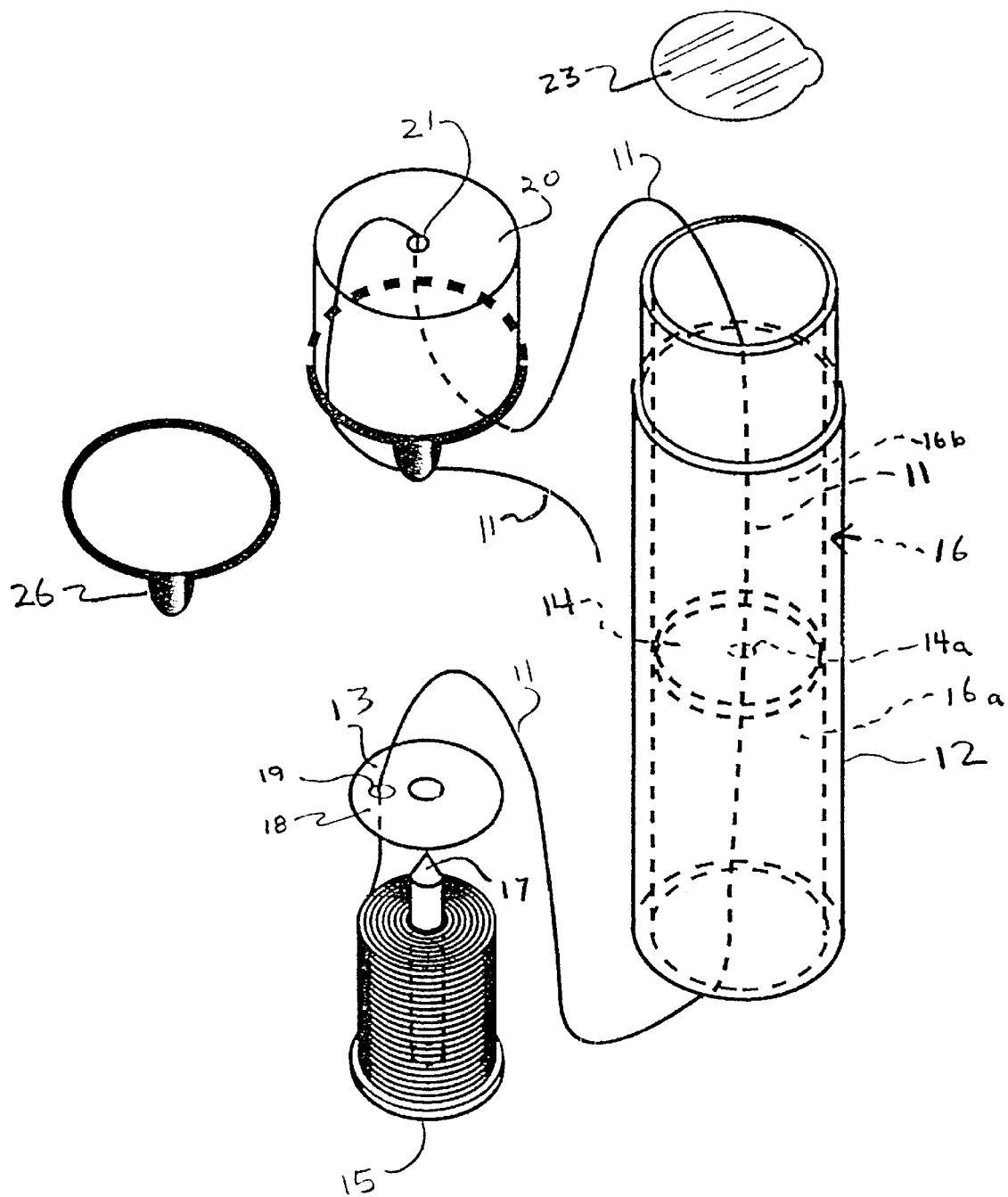
FIG. 2 is an exploded view the dispenser of FIG. 1.
Figure 3:
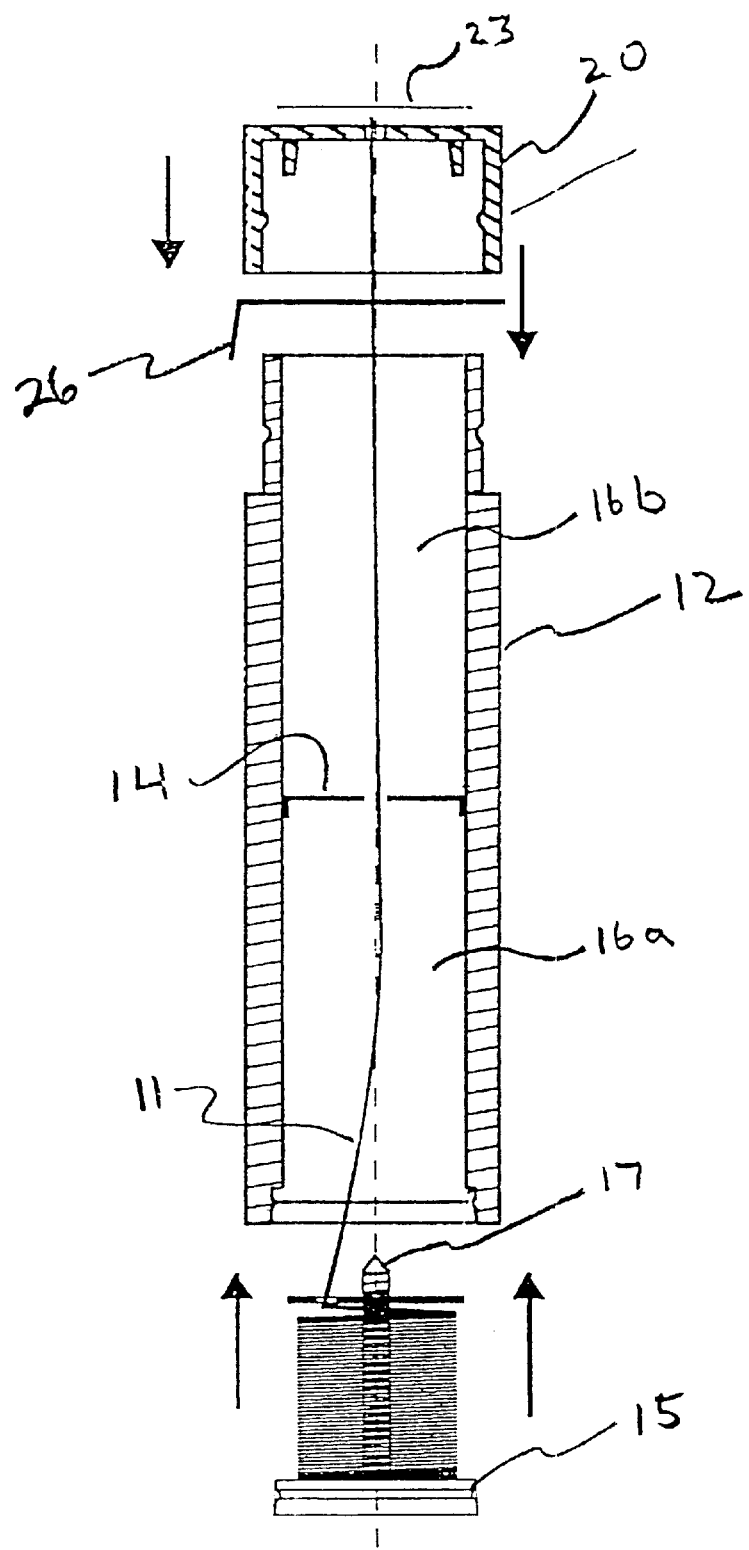
FIG. 3 is a view of cross-sectional, partially exploded view the dispenser of FIG. 1 showing the assembly thereof.

Turning now to the drawings throughout the several views, FIGS. 1 through 3 illustrate a treated floss dispenser 10 including a tube 12 that holds base 15, with floss 11 coiled on a shaft 17. The coiled floss is separated from the main chamber 16 defined by tube 12 by separator 8, which may be a disc or a bag. The main chamber 16 may consist of one of several compartments 16a, 16b and it is filled with fluids and or solids. The floss 11 is first threaded through a hole 19 in the protective cover 13 that separates the floss reel 15 from the lower compartment 16a. Opening 19 in cover 13 can be approximately twice the width of the untreated floss 11. Floss 11 passes through the lower compartment 16a filled with a viscous fluid. The partially impregnated floss is then threaded through opening 14a in barrier 14 that divides the lower and upper compartments 16a, 16b. Opening 14a can be approximately twice the width of the untreated floss 11. The floss 11 then passes through the upper compartment 16b filled with an impregnating fluid or solid. The fluids and/or solids are now adhered to the floss 11 so it can be used as a means to deliver those compositions between and onto a user's teeth. The impregnated floss 11 is then threaded through a wiping hole 21 in the cap 20 of the dispenser. A pressure fitted or threaded cap is preferred to avoid any potential fluid leaks. The opening 21 is sealed by adhesive backed plastic, paper or foil 23 preventing fluid loss and the accidental dispensing of the floss. A cutter 26 is placed on the neck of the container 12 and it is used for removing a segment of the impregnated floss 11.

The tube 12, cap 20, base 15 and shaft 17 are preferably fabricated out of durable plastic materials and the cutter 26 is preferably metal or a hard plastic. However, other types of material can be used such as cardboard, wood, etc. The floss 11 is preferably fabricated of highly absorbent , un-waxed string of a diameter suitable for inter-dental flossing.

One or both of chambers 16a, 16b are filled with a composition to be applied to the floss. The compositions provide a means for applying a useful material to the floss just prior to delivery. Useful materials include medicaments, cleansers, breath fresheners, etc. Particularly useful materials to be applied to the floss include alkali metal bicarbonate, hydrogen peroxide and fluoride. Because the compositions are physically separated from each other, it is possible to fill chambers 16a, 16b with chemically incompatible materials which are brought together only at the moment of withdrawing floss from the dispenser. Chambers 16a, 16b can both be filled with fluid compositions, preferably highly viscous fluids or gels to avoid spillage of the composition from the dispenser.

In a particularly useful embodiment, lower chamber 16a is filled with a first composition, such as, for example, a viscous gel or paste. The untreated floss 11 passes through the first composition and is impregnated therewith. The partially treated floss 11 is then threaded through the divider 14. The opening 14a, which should be slightly larger than the untreated floss 11, will have a leveling effect on any excess amount of the first composition on the floss 11. The partially treated floss 11 then passes through upper chamber 16b which is filled with a second composition, such as, for example, a particulate solid material. The solid particles will adhere to the surface of the previously impregnated floss 11. The completely treated floss 11 can then be dispensed through cap 20 and a desired length removed via cutter 26. An adhesive backed seal or foil 23 is placed on top of cap 20 of the assembled and filled components.

Example 1 provides illustrative compositions of a first composition which is a viscous gel and a second composition which is a solid (in this example a powder).

| First Composition Components | w/w % |
|---|---|
| Water | 71.0 |
| Poloxamer 407 | 5.0 |
| Hydrogen Peroxide (3% sol'n) | 20.0 |
| Glycerin | 3.0 |
| Flavor | q.s. |
| Phosphoric Acid | q.s. |
| | 100.00 | viscosity > 250,000 centipoise
pH 3.5

| Second Composition Components | w/w % |
|---|---|
| Sodium Bicarbonate | 99.3 |
| Fumed Silica | 0.5 |
| Sodium Fluoride | 0.2 |
| | 100.00 |

When unwaxed floss is dispensed through the gel of Example 1 and threaded through a hole in divider 14 of twice the width of the untreated floss, the weight/unit length of the treated floss remains constant regardless the length of the path through the lower chamber. For example, when using unwaxed and untreated floss 11 having a fineness of 90 mg/m (milligram per meter) the total weight of partially impregnated floss is 190 mg/m. That is 90 mg of string and 100 mg of gel per meter. When the partially impregnated floss passes through the solid in the upper compartment 16b of tube 12, the total weight increases to 240 mg/m, that is an increase of 50 mg/m due to the solid particles attached to the surface of the gel. The tack and feel of the floss are very functional and acceptable.

The viscosity of the fluid applied to the floss will determine the wetting characteristics of the fluid. That is, the viscosity of the fluid will affect the degree of permeation of the fluid into the untreated floss. Thus, for example, when the viscosity of the gel in Example 1 is lowered to 10,000 centipoise, the floss weight/m doubles and increases the tack and wetness of the string. These are not desirable characteristics for the patient handling of the floss. When the viscosity of fluid is only a few centipoise, the floss has a low tack and acceptable characteristics, however, the fluid will flow into the upper chamber during the handling and use of the product, creating compatibility and dispensing problems. Thus, in preferred embodiments, the composition of the fluid applied to the floss has a viscosity in the range of about 50,000 cp to about 1,000,000 cp. In particularly preferred embodiments, the fluid is formulated to be a substantially non-flowing gel.

Figure 4:
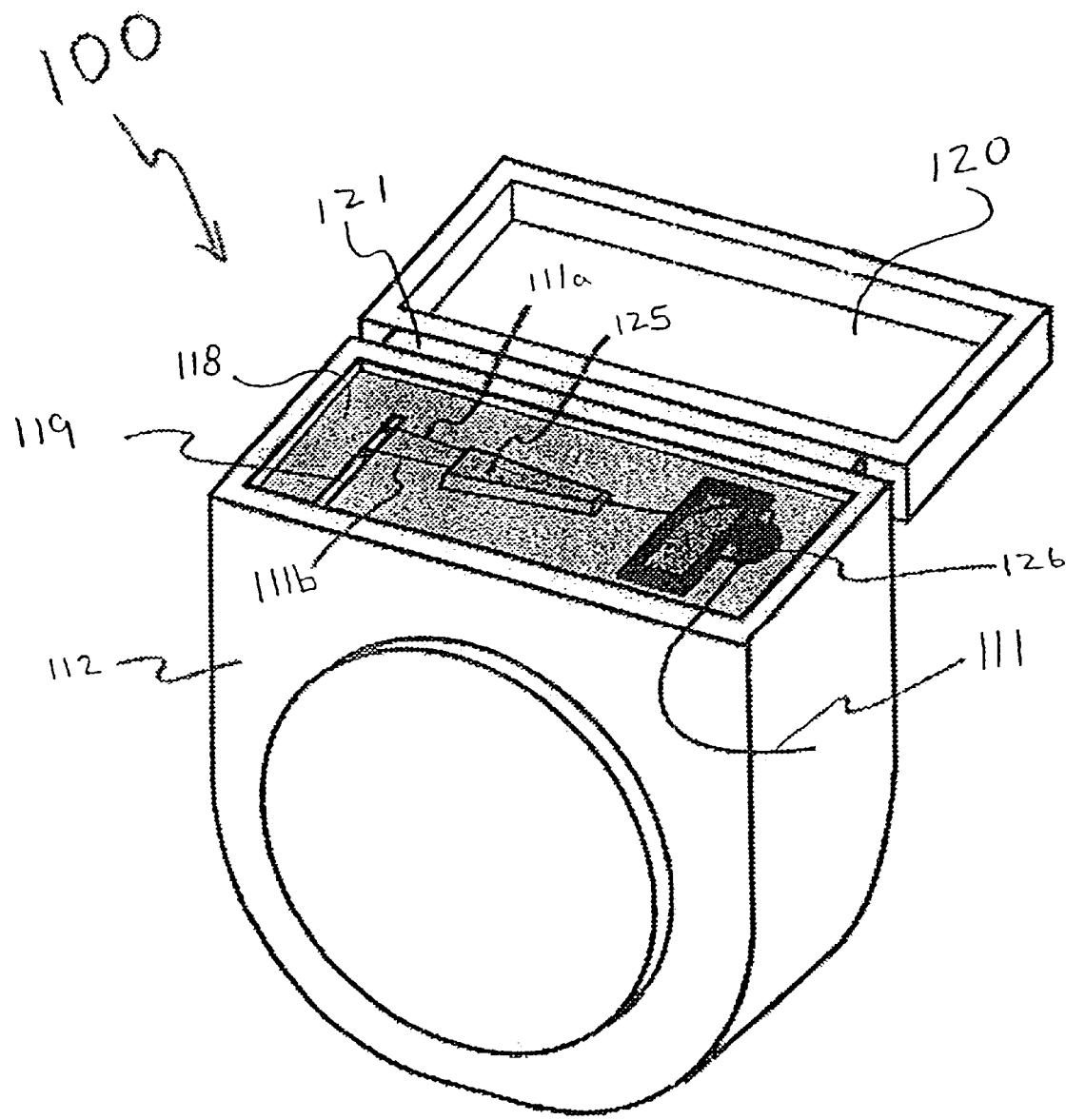
FIG. 4 is a perspective view of an alternative embodiment of a treated floss dual dispenser in accordance with this disclosure.
Figure 4A:
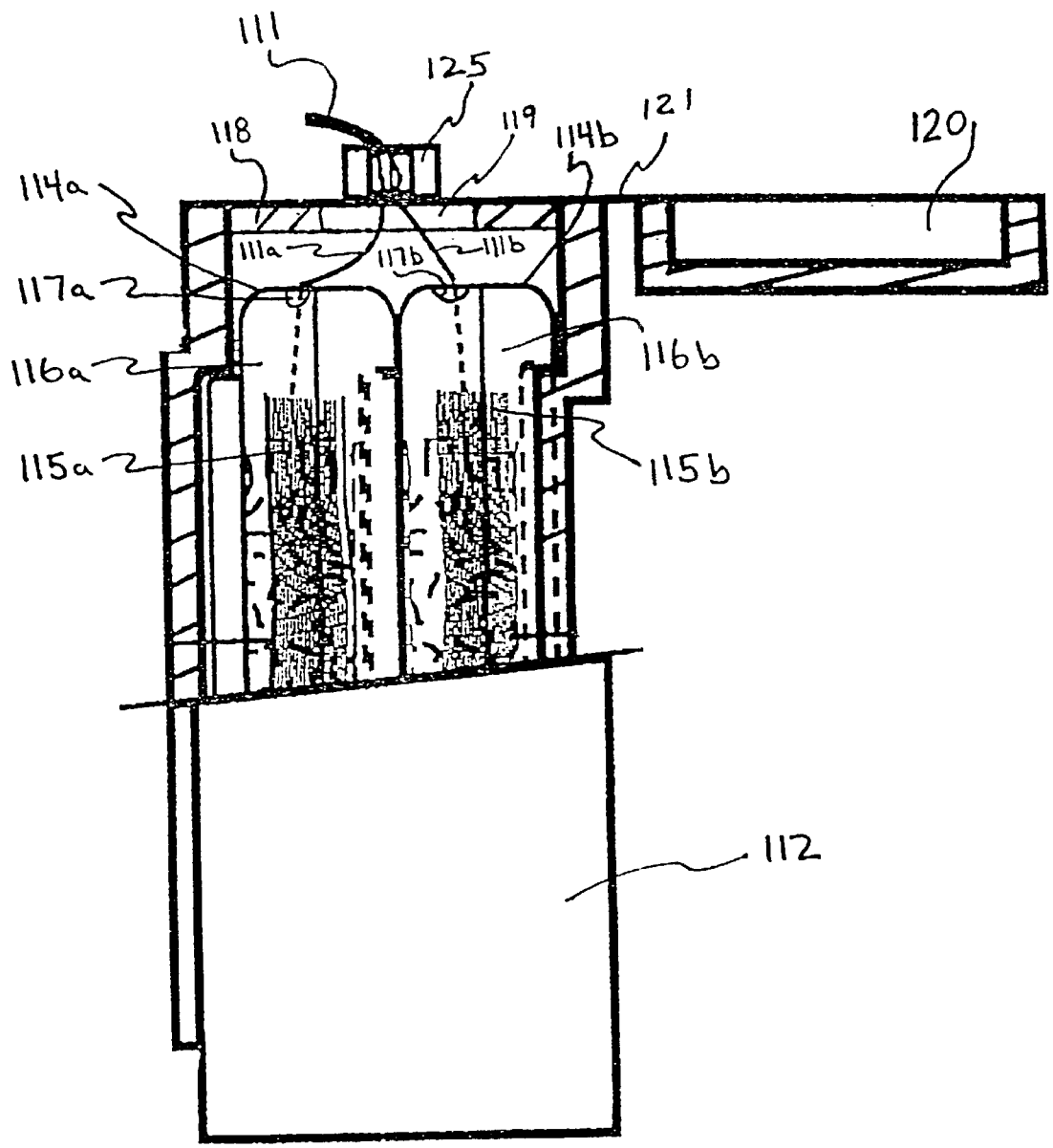
FIG. 4A is a side, partially cross-sectional view of the dispenser of FIG. 4.

FIG. 4 illustrates an alternative embodiment of a floss dispenser in accordance with this disclosure which is a treated floss dual dispenser. FIG. 4A illustrates the floss dual dispenser which includes two separate containers 114a, 114b within a housing 112. Each container contains a supply of dental floss 115 in a chamber 116 that can be filled with a composition to be applied to the floss. Suitable compositions for use in this embodiment are those described above with respect to the previous embodiment.

Figure 5A:
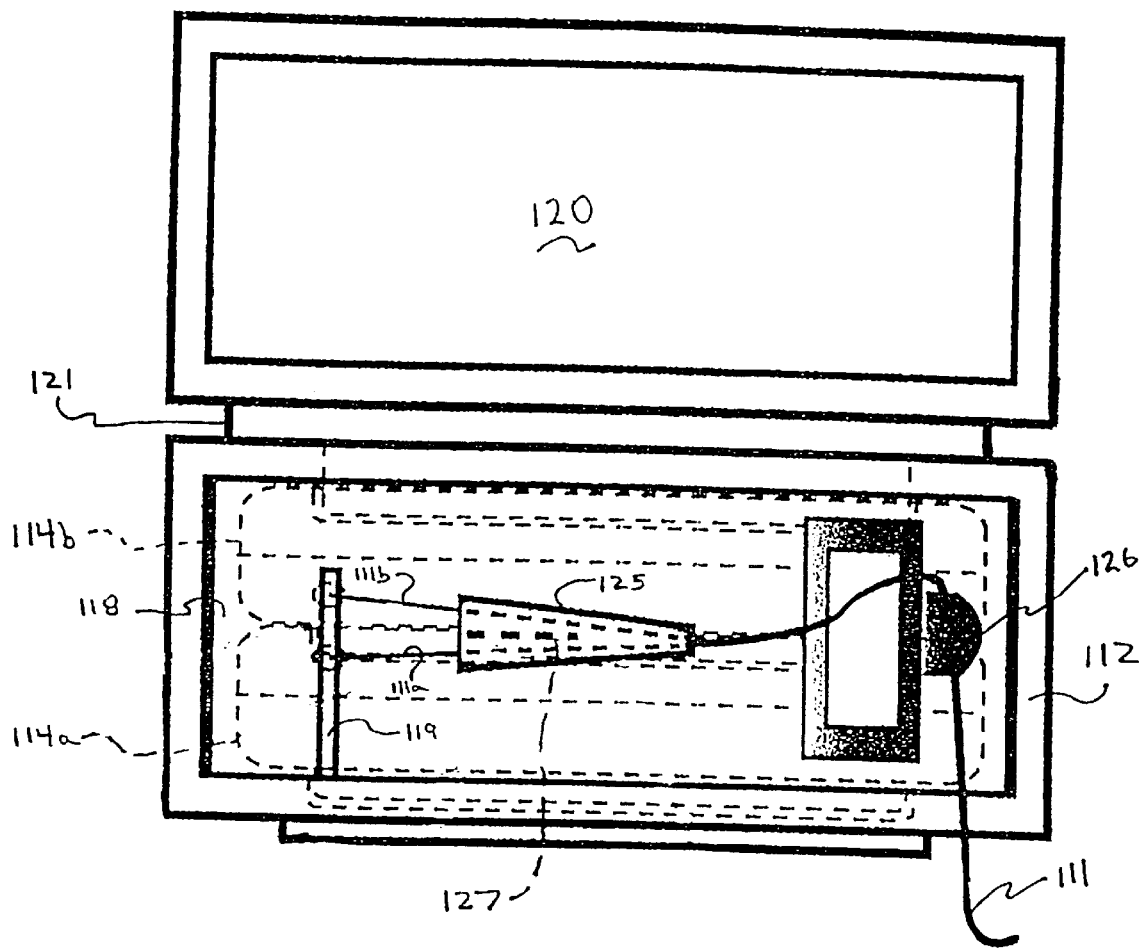
FIGS. 5A and 5C show front and top views, respectively of the dispenser of FIG. 4.
Figure 5B:
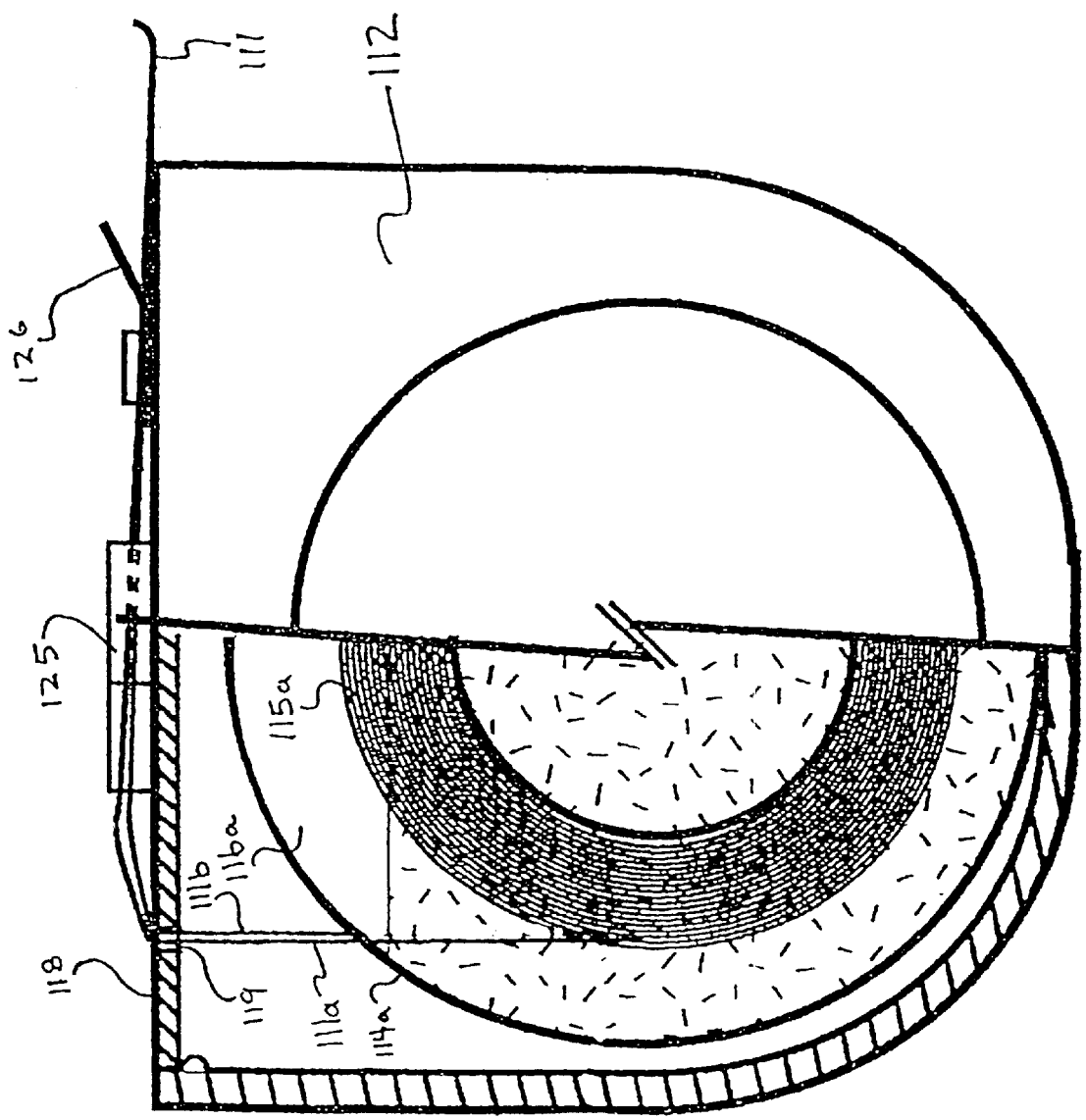
FIG. 5B is a side, partially cross sectional view of the dispenser of FIG. 4.
Figure 5C:
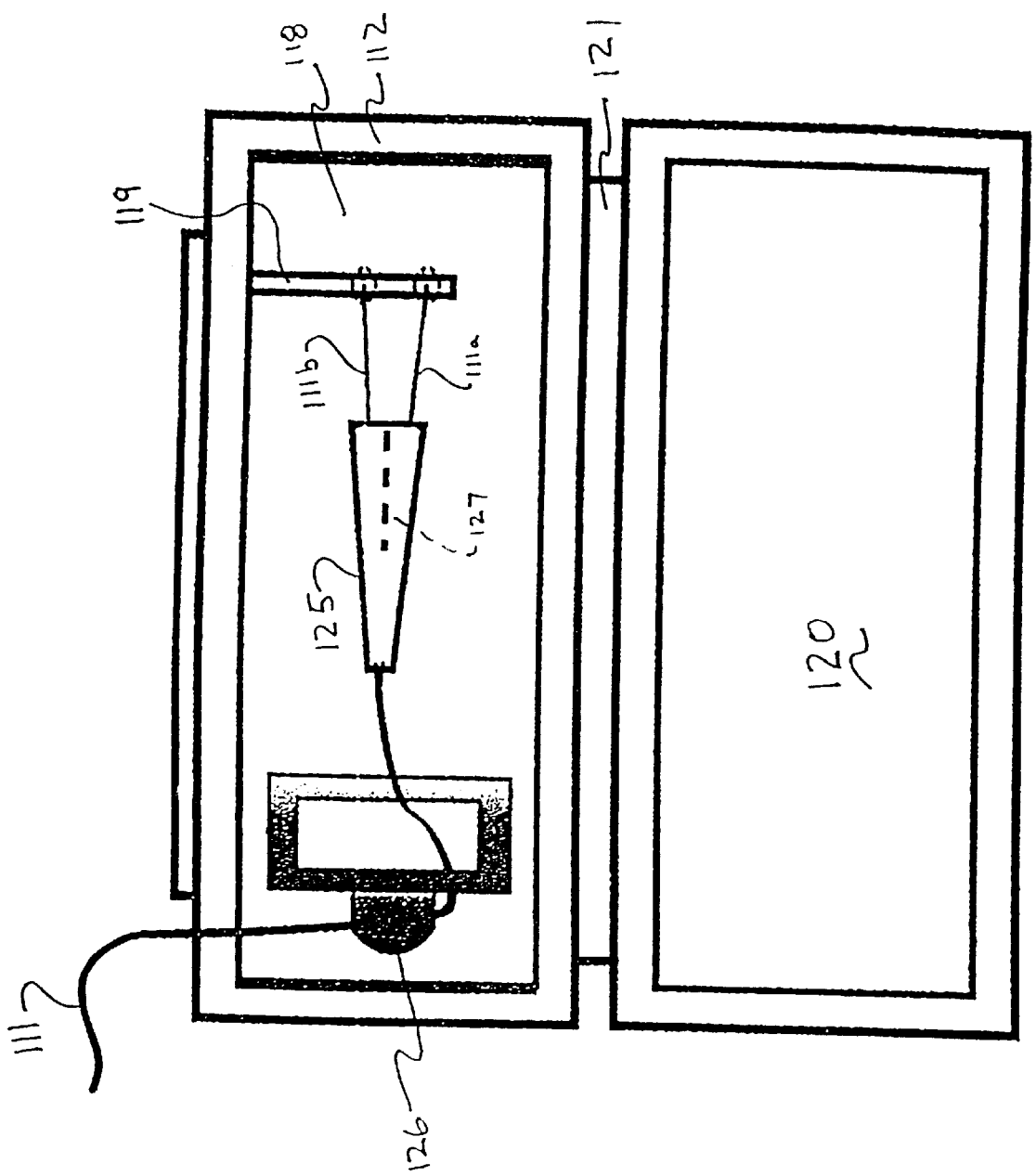

FIGS. 5A and 5B illustrate the internal components of each container 114a, 114b with the floss 111 in contact with first and second compositions, respectively. The separate flosses 111a, 111b are individually impregnated as they are dispensed through orifices 117a, 117b of each container 114a, 114b. Orifices 117a, 117b can advantageously made to be twice the width of the floss. As seen in FIGS. 5A and C, the individually impregnated flosses pass through opening 119 in top 118 of housing 112 and are threaded through funneling tube 125 which serves as a means for urging the individually impregnated floss strands 111a, 111b into contact with each other. In this manner the individually impregnated floss strands 111a, 111b are adhered to each other to form a unitary dual treated floss 111. Funneling tube 125 includes a divider 127 to keep the individually impregnated floss strands 111a, 111b separated from each other prior to being dispensed. The unitary dual treated floss 111 can be cut into segments of desired length using cutter 126. The segment impregnated with the adhered compositions can be utilized for whitening the teeth and for the treatment of gingivitis. Cover 120, which is joined to housing 112 by living hinge 121, encloses the floss between uses.

Example 2 provides illustrative first and second compositions which are a gel and a paste, respectively, for use in the dual dispenser of FIGS. 4, 4A and 5A–C.

| First Composition Components | w/w % |
|---|---|
| Water | 74.00 |
| Hydrogen Peroxide (30% solution) | 20.00 |
| Poloxamer 407 | 5.00 |
| Glycerin | 3.00 |
| Flavor | q.s. |
| Phosphoric Acid | q.s. |
| | 100.00 | viscosity > 250,000 centipoise
pH 3.75

| Second Composition Components | w/w % |
|---|---|
| Water | 43.00 |
| Glycerin | 25.00 |
| Sodium Bicarbonate | 25.00 |
| Nonionic Cellulose Gum | 6.00 |
| Flavor | q.s. |
| Preservative | q.s. |
| | 100.00 |

Viscosity > 250,000 centipoises
pH 7.0

Floss having a fineness of 100 mg/m is passed through the two compositions of Example 2, to provide individually impregnated flosses having a total weight of 190 mg/m each. The individually impregnated flosses are then threaded and passed through the funneling tube where they adhere to each other. The joined floss has a total weight 380 mg/m. The amount of the first and second compositions impregnated onto the individual flosses depends on a number of factors including the affinity of the composition for the thread and the viscosity of the composition. The residual amount left on the impregnated flosses after being dispensed can also be changed by adjusting the diameter of orifices 117a, 117b. Twice the width of the floss works well when using gels and pastes in the>250,000 centipoise range.

While certain features of this invention have been shown and described and are pointed out in the claims, it will be understood that changes in the forms and details of the dispenser can be made by those skilled in the art without departing from the spirit of the invention.

What is claimed is:
1. A dental floss dispenser comprising:
   a) a housing having an opening through which dental floss can be dispensed;
   b) a first container positioned within the housing, the first container containing a first supply of dental floss and a first composition in contact with the first supply of dental floss;
   c) a second container positioned within the housing, the second container containing a second supply of dental floss and a second composition that is chemically different from the first composition, the second composition being in contact with the second supply of dental floss; and
   d) means for urging floss from the first supply of dental floss into contact with floss from the second supply of dental floss prior to being dispensed through the orifice in the housing.
2. A dental floss dispenser as in claim 1 wherein the first and second compositions is are each fluids having a viscosity in the range of about 50,000 cp to about 1,000,000 cp.
3. A dental floss dispenser as in claim 1 wherein one of the first or second compositions contains a hydrogen peroxide.
4. A dental floss dispenser as in claim 1 wherein one of the first or second compositions comprises an alkali metal bicarbonate.
5. A dental floss dispenser as in claim 1 wherein one of the first or second composition contains fluoride.
6. A dental floss dispenser as in claim 1 further comprising a cutter for dividing the dispensed floss into segments of a desired length.
7. A dental floss dispenser as in claim 1 further comprising a cap enclosing the opening in the housing through which floss is dispensed.

* * * * *